United States Patent [19]

Dvorsky

[11] Patent Number: 4,869,101
[45] Date of Patent: Sep. 26, 1989

[54] TEXTURE SOFTNESS SENSING

[75] Inventor: James E. Dvorsky, Columbus, Ohio

[73] Assignee: Battelle Memorial Institute, Columbus, Ohio

[21] Appl. No.: 219,257

[22] Filed: Jul. 15, 1988

[51] Int. Cl.$^4$ ............................................. G01N 19/00
[52] U.S. Cl. ...................................... 73/159; 73/573; 73/78
[58] Field of Search ................... 73/78, 159, 573; 381/173, 190

[56] References Cited

U.S. PATENT DOCUMENTS

| | | | |
|---|---|---|---|
| 2,752,781 | 7/1956 | Thorsen | 73/159 |
| 2,922,303 | 1/1960 | Veneklasen et al. | 73/159 |
| 3,683,681 | 8/1972 | Taylor | 73/78 |
| 4,379,211 | 4/1983 | Joscelyn et al. | 381/173 |
| 4,548,081 | 10/1985 | Wolthausen | 73/159 |
| 4,607,145 | 8/1986 | Ravinet et al. | 381/190 |
| 4,735,087 | 4/1988 | Haurani et al. | 73/159 |

Primary Examiner—Allan N. Shoap
Assistant Examiner—Jeffrey J. Hohenshell
Attorney, Agent, or Firm—Watkins, Dunbar & Pollick

[57] ABSTRACT

Apparatus and method for use in measuring the softness of a fibrous product comprises a piezoelectric polymer film sensor, preferably polyvinylidene (di)fluoride with adhered opposed electrode surfaces, a sample of the fibrous product in direct contact with one of the sensor electrode surfaces, acutation components acoustically activating the fibrous product sample to cause the film sensor to generate an output electrical signal, and a spectrum analyzer for characterizing the fibrous product softness from the output electrical signal.

16 Claims, 2 Drawing Sheets

TEXTURE SOFTNESS SENSING

FIELD OF INVENTION

The present invention relates generally to texture softness sensing, and particularly concerns new improved apparatus and methods for quantitatively characterizing the degree of softness of surfaces of certain materials such as the surfaces of paper or textile products.

BACKGROUND OF THE INVENTION

In the promotion of many paper or textile products such as personal care products, the perceived texture and softness of the product by the consumer is important for its general acceptance and use. To obtain this desired texture and softness, a condition that is usually loosely defined and difficult to describe, manufacturers expend considerable time and effort adjusting their manufacturing process to produce materials with a fiber content, size, and dispersion that ultimately "feels soft" in the final product. Often, the determination of texture and softness is accomplished by a team of human evaluators who touch and manipulate product samples to evaluate the quality and acceptability of the material. While the judgment is mostly qualitative, this typical approach to quality assurance has generally worked well in the past.

Unfortunately, the use of human evaluators has a number of limitations. The decision of whether or not a material has an acceptable texture and softness is largely qualitative, and the number of process variables involved in achieving this softness is large. Often it is difficult, without considerable analysis, to precisely locate operations within the manufacturing process that may require adjustment. Furthermore, because human beings are subject to sickness, emotional stress, and dermatological ailments, among others, the judgment of texture or softness made by the evaluation team is not always accurate and repeatable. This fluctuation in judgment can be detrimental to the manufacturer in two ways: (1) If good material is judged as unacceptable, considerable time and resources are needlessly wasted in trying to correct the situation. (2) More importantly, if poor material is judged as acceptable, the product may eventually be rejected by the consumer, adversely affecting the manufacturer's reputation.

The need for developing an integrated softness parameter much like the numerical scoring techniques used to rank standard paper tissue or textile product softness is accordingly apparent. Such may be accomplished by monitoring the dynamic characteristics of two similar samples when they are gently rubbed together, and advances in sensing technology and signal processing offer solutions to the problem.

The prior art of softness sensing, particularly of textile materials, contains several examples of materials that are rubbed to generate an acoustic emission, which in turn is evaluated to determine the characteristics of the material being tested. One approach is described by Thorsen in "Apparatus for Determining Textile Characteristics" (U.S. Pat. No. 2,752,781), where two similar materials under test are rubbed against each other and the acoustic output is monitored with a vibrating diaphragm and contact microphone. A similar approach is described by Veneklasen, et al, in "Acoustic Testing Instrument" (U.S. Pat. No. 2,922,303) but relies on fluid coupling to transmit the acoustic signals. In Taylor's patent entitled "Method and Apparatus for Softness Testing" (U.S. Pat. No. 3,683,681), a third approach, specifically designed for measuring softness of paper fabric materials, is disclosed.

In the Thorsen patent, vibration resulting from two similar materials drawn across each other is transmitted through a cardboard diaphragm to a contact microphone. Several means of vibration isolation are employed, and the entire measuring apparatus is surrounded by sound absorbing material to reduce the effects of ambient noise.

The texture softness sensing approach disclosed in this application also relies on mutual motion between two materials under test, but the sensing element is a flexible piezoelectric polymer that is in intimate contact with the materials. By using this technique, the sensitivity to acoustic vibration in the tested materials is maximized, and minimal means of vibration isolation are required. In addition, while the sensor is capable of detecting some ambient noise, the configuration is non-optimum for this mode of detection. The net result is that ambient conditions have minimal effect on the measurement technique, and little if any means of acoustic shielding are needed.

The sensing approach was principally designed to measure the surface characteristics of tissue paper products, but it may also be applied to textile materials with equal validity.

Finally, the disclosed technique is designed to measure surface characteristics of pliable materials, in particular surface softness. But, the principal material parameter measured by the approach described by Taylor is generally referred to as bulk softness. Bulk softness is a characteristic of paper and textile products that relates to the perceived stiffness, density, and general handling of the material. Furthermore, the methods of measurement are varied. Taylor's apparatus consists of multiple rolls that massage and distort the bulk features of the materials under test so that acoustic emissions are generated and detected by a remotely place microphone. In the texture sensing approach described here, surface softness is measured using an intimately contacting acoustic sensor.

SUMMARY OF THE INVENTION

A sensor system is configured to advantageously utilize a shielded piezoelectric polymer film sensor (with opposed conducting electrodes) either firmly held in tension or firmly adhered to the surface of a base platform. A shielded cable conductor connects the film sensor electrodes to a spectrum analyzer. Either two randomly selected specimens of an object sample to be tested or one specimen and a surface having known roughness are utilized. In one embodiment of the invention, one specimen is positioned over the sensor and its edges are secured to the base platform so that the specimen is in intimate contact with the sensor. The other specimen is adhered to the underside of a small, flat, rigid, light-weight carrier platform. A cord is fastened to the edge of the carrier platform and to the shaft of a constant speed motor having a slow rate of rotation. The carrier platform and specimen assembly is placed on the specimen/sensor combination, so that the two specimens are in contact and a known weight is placed on the carrier platform to apply a known constant pressure to the two specimens. Other force generating arrangements can be utilized. The tray/specimen components are slowly drawn across the surface of the specimen/sensor combination and the vibration/acoustic output detected by the film sensor. In response, the sensor generates an electrical signal that is delivered to a spectrum analyzer where it is processed and subsequently displayed for viewing or recording.

Other embodiments of the invention are also disclosed, particularly an "online" production sensor system and also systems utilizing a tensioned sensor film.

The foregoing and other advantages of the invention will become apparent from the following disclosure in which a preferred embodiment of the invention is described in detail and illustrated in the accompanying drawings. It is contemplated that variations in structural features and arrangement of parts may appear to the person skilled in the art without departing from the scope or sacrificing any of the advantages of the invention.

DETAILED DESCRIPTION OF THE INVENTION AND PREFERRED BEST MODE OF EMBODIMENT

Figure 1:
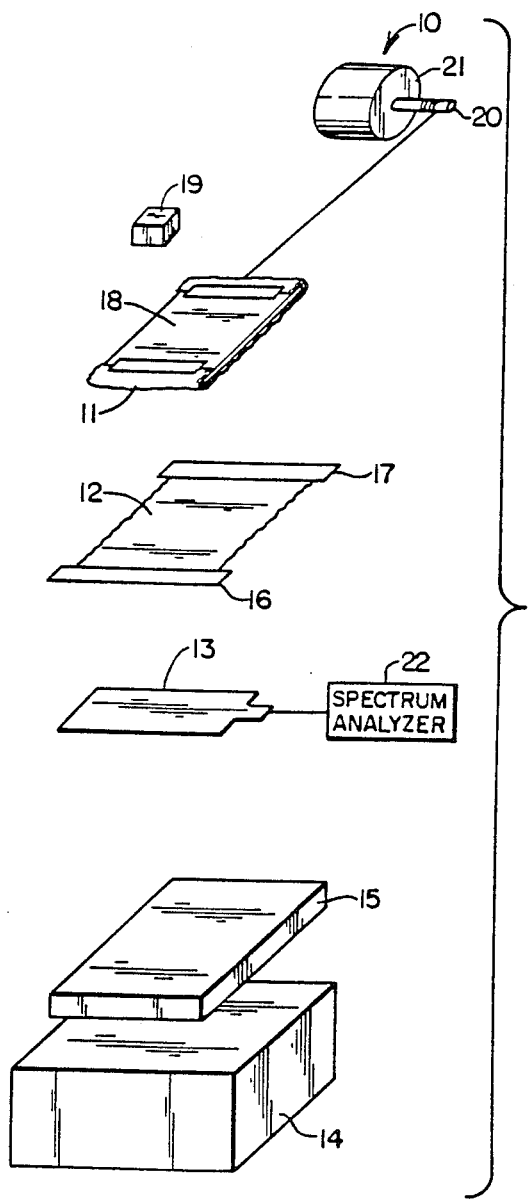
FIG. 1 is an exploded perspective view of the principal elements of the present invention in their normal assembled relation.

Referring to FIG. 1 of the drawings, assembly 10 is illustrated in exploded relationship and is utilized for quantitatively measuring the softness characteristic of a fibrous product such as tissue paper specimens 11 and 12 or the like. The softness is measured using a piezoelectric sensor means 13 which preferably is comprised of polyvinylidene (di)fluoride film with adhered electrode films at its opposite surfaces. One satisfactory electrode film material is an applied silver paint although other conductive coatings such as electro-deposited nickel-aluminum would be satisfactory. The base of the apparatus 14 is a vibration isolating material which supports base platform 15; base platform 15 is preferably a rigid material. Bonding adhesive or other suitable means used to secure film sensor means 13 to the upper surface of base platform 15. Superimposed above the vibration isolation base 14, base platform 15, and piezoelectric polymer film sensor means 13 is fibrous product specimen 12 which is bonded to the surface of base platform 15 by means of tape strips 16 and 17 or other suitable means. A lightweight carrier platform 18 is utilized to support specimen 11 and a known weight 19. Fibrous product specimen 11 is secured to the underside of carrier platform 18 and such is accomplished using tape or other suitable means similar to masking tape strips 16 and 17. Carrier platform 18 is connected by a flexible line to shaft 20 of induction gear motor 21 or other constant speed motor. Gear motor 21 is selected so that the carrier platform 18 and its attached specimen 11 are drawn across the base platform 15, sensor 13, and specimen 12 at a constant velocity of approximately five inches per minute. Piezoelectric polymer film sensor means 13 is connected to a spectrum analyzer 22 such as a Hewlett-Packard Model 3582A Spectrum Analyzer by means of a shielded cable.

Figure 2:
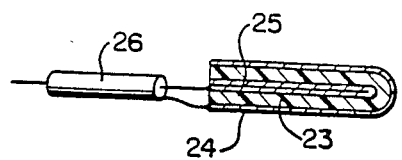
FIG. 2 is a cross sectional view of a shielding technology incorporated into the piezoelectric polymer film sensor element of this invention.

The piezoelectric sensor 13, which has conductive films 24 and 25 at opposite sides of piezoelectric polymer film 23, may be folded over upon itself as shown in FIG. 2 to provide a shielded sensor. The outer conductor film 24 is grounded and the inner doubled electrode film 25 provides the sensor output signal.

Figure 3:
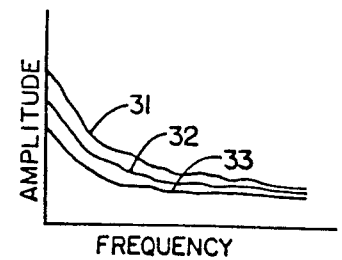
FIG. 3 is a composite graph showing the measured softness characteristics of three different samples of a soft paper tissue.

FIG. 3 illustrates three curves 31, 32, and 33 that were developed and plotted to measure the softness of three different paper tissue samples. The figure presents signal amplitude versus frequency, where amplitude is displayed logarithmically in decibels. Curve 31 is for a coarse textured tissue, curve 32 is for a medium soft tissue, and data curve 33 is for a very soft tissue. All data was developed utilizing the apparatus illustrated in exploded relationship in FIG. 1.

Figure 4:
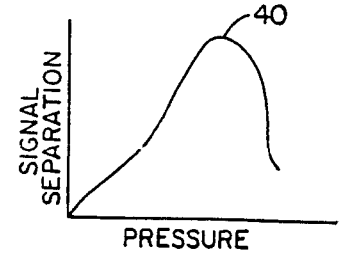
FIG. 4 is a graph showing the effect of weight upon sensor electrical output signal separation.

FIG. 4 is a graph showing the relationship which exists between the weight of carrier platform 18 (and included weight 19) and the signal separation which exists as between coarse and soft tissues (e.g. curves 31 and 33, FIG. 3). Weight 19 is experimentally increased in size until an optimum weight is reached which produces a maximum sensor response and signal-to-noise ratio. Subsequent tests use the weight of the optimum level. Excess applied weight tends to dampen the output signals and reduce the separation between traces. For certain paper tissue samples, an ideal weight of four ounces was determined for one apparatus arrangement.

Figure 5:
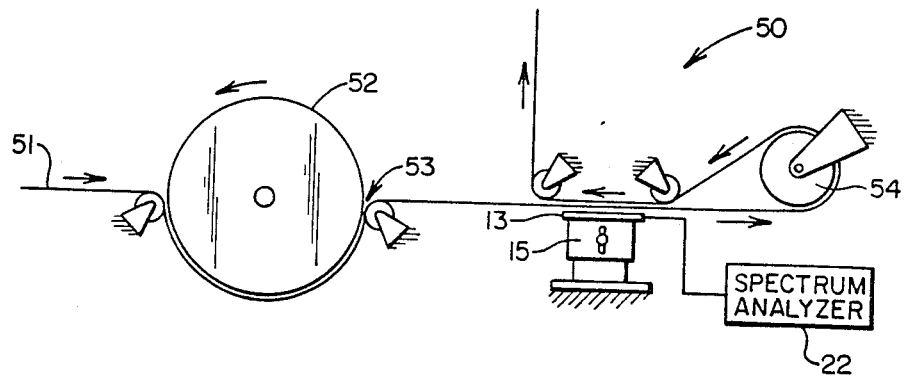
FIG. 5 is a schematic illustration of the present invention applied to a continuous production process.

FIG. 5 schematically illustrates the present invention as applied to apparatus 50 for the continuous production of a web 51 of fibrous paper tissue. Web 51 first passes under a portion of drier drum 52 and is afterwards separated from drum 52 by knife edge 53. The separated and creped web, which has opposite felted and dryer surfaces, then passes over piezoelectric sensor 13 supported by adjustable base platform 15. After passing over roller 54, the web is reversed upon itself and is passed in contact with the dryer surface of the web at sensor 13. The pressure applied between the contacting portions of web 51 at sensor 13 may be varied by adjusting the height of base platform 15.

Figure 6:
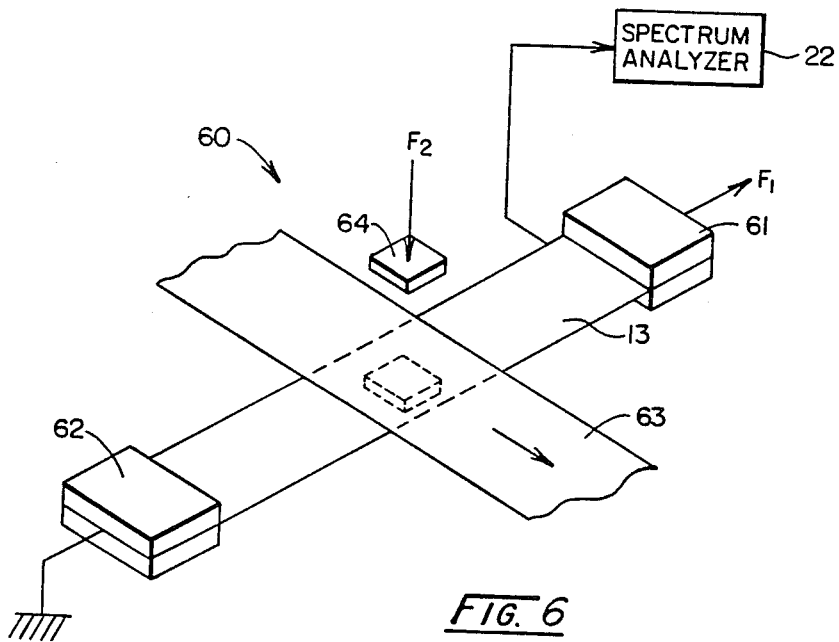
FIG. 6 is a schematic illustration of the present invention applied to a continuous production process with emphasis on use of a tensioned sensor film and a reference roughened surface for generating acoustic vibrations from the object sample specimen.

FIG. 6 illustrates schematically a still further embodiment of the present invention and such is designated as 60 in the drawings. In such embodiment the piezoelectric polymer film sensor 13 is clamped at its opposed ends in the conventional clamping devices designated 61 and 62. A constant force F and a reaction force are applied to clamps 61 and 62 to maintain sensor 12 in a firm, taut condition. Tensioned sensor 13 is connected to spectrum analyzer 22 in the manner previously discussed.

In the FIG. 6 arrangement the fibrous specimen 63 is maintained in sliding contact with the upper surface of sensor 13 as the specimen is advanced laterally (and orthoganally relative to the tensile forces of sensor 13) as in a continuous production process. The acoustic vibrations developed in specimen 63 for sensing by sensor 13 are developed by moving the underside roughened reference surface of standard specimen block 64 downwardly with sufficient force to develop the desired contact pressure between block 64, specimen 63, and tensioned sensor film 13. This arrangement appears to be particularly well-suited to a continuous production process.

It is herein understood that although the present invention has been specifically disclosed with the preferred embodiments and examples, modifications and variations of the concepts herein disclosed may be resorted to by those skilled in the art. Such modifications and variations are considered to be within the scope of the invention and the appended claims.

I claim:

1. Apparatus for characterizing the degree of softness of a thin fibrous sample, comprising
   (a) piezoelectric polymer film sensor means with opposed conducting surface films;
   (b) a specimen of a thin fibrous sample in direct contact with said piezoelectric polymer film sensor means;
   (c) a reference surface contacting said specimen of a thin fibrous sample;
   (d) means of applying a known constant force between said piezoelectric polymer film sensor means, said specimen of a thin fibrous sample, and said reference surface;
   (e) means for producing relative motion between said specimen of a thin fibrous sample and said reference surface; and
   (f) means for analyzing an electrical output signals produced by said piezoelectric polymer film sensor means over a wide-band frequency spectrum to characterize the surface softness of said specimen, whereby said output electrical signal is produced by said piezoelectric polymer film sensor means when said specimen of a thin fibrous sample and said reference surface are moved relative to each other thereby inducing vibration in said specimen of a thin fibrous sample and said piezoelectric polymer film sensor means; said output electrical signal being correlated with minimal acoustic amplitude attenuation to the softness of said specimen of a thin fibrous sample.

2. The apparatus defined by claim 1 wherein said piezoelectric polymer film sensor means comprises polyvinylidene (di)fluoride.

3. The apparatus defined by claim 1 further comprising base platform means having a relatively rigid upper surface, said piezoelectric polymer film sensor means being supported by and adhered to said platform means upper surface;

4. The apparatus defined by claim 1 wherein said piezoelectric polymer film sensor means is supported by and tensioned between opposed forces applied to said sensor means.

5. The apparatus defined by claim 1 wherein said reference surface comprises a second specimen of said thin fibrous sample.

6. The apparatus defined by claim 1 wherein said reference surface comprises a surface having a known roughness.

7. The apparatus defined by claim 1 further comprising a spectrum analyzer and shielded cable means connecting said spectrum analyzer to said piezoelectric polymer film sensor means.

8. The apparatus defined by claim 5 wherein said means of applying known constant force causes the greatest difference in amplitude of wide band output signals associated with said first and second specimen of the thin fibrous samples.

9. A method of characterizing the degree of softness of a specimen of a thin fibrous sample, comprising the steps of
   (a.) providing a piezoelectric polymer film sensor means with opposed conducting surfaces films;
   (b.) placing a specimen of a think fibrous sample in direct contact with said piezoelectric polymer film sensor means;
   (c.) placing a reference surface in contacting relation to said specimen of a thin fibrous sample;
   (d.) applying a known constant force between said piezoelectric polymer film sensor means, said specimen of a thin fibrous sample, and said reference surface;
   (e.) producing relative motion between said specimen of a thin fibrous sample and said reference surface to cause said piezoelectric polymer film sensor means to generate an electrical output signal which correlates without acoustic amplitude attenuation to the softness of said specimen of a thin fibrous sample; and
   (f.) characterizing the softness of the specimen of a thin fibrous sample from analysis of said electrical output signal of said piezoelectric polymer film sensor means over a wide-band frequency spectrum.

10. The method defined by claim 9 wherein said piezoelectric polymer film, sensor means comprises polyvinylidene (di)fluoride.

11. The method defined by claim 9 wherein said provided piezoelectric polymer film sensor means is supported by and adhered to a relatively rigid base platform means.

12. The method defined by claim 9 wherein said piezoelectric polymer film sensor means is supported by and tensioned between opposed forces applied to said sensor means.

13. The method defined by claim 9 wherein said reference surface comprises a second specimen of said thin fibrous sample.

14. The method defined by claim 9 wherein said reference surface comprises a surface having a known roughness.

15. The method defined by claim 9 further comprising providing a spectrum analyzer and shielded cable means connecting said spectrum analyzer to said piezoelectric polymer film sensor means.

16. The method defined by claim 13 wherein said means of applying known constant force causes the greatest difference in amplitude of wide band output signals associated with said first and second specimen of the thin fibrous samples.

* * * * *